United States Patent [19]
Day

[11] Patent Number: 6,155,261
[45] Date of Patent: Dec. 5, 2000

[54] METHOD AND APPARATUS FOR RELIEVING INTRAOCULAR PRESSURE

[76] Inventor: Daniel K. Day, 4513 Edina Blvd., Edina, Minn. 55424

[21] Appl. No.: 09/273,903

[22] Filed: Mar. 22, 1999

[51] Int. Cl.$^7$ ....................................................... A61F 13/00
[52] U.S. Cl. ............................................ 128/846; 128/858
[58] Field of Search ................................... 128/845, 846, 128/857, 858; 2/15, 433, 439, 446, 448, 454

[56] References Cited

U.S. PATENT DOCUMENTS

| | | | |
|---|---|---|---|
| 2,891,252 | 6/1959 | Lazo | 2/15 |
| 4,271,538 | 6/1981 | Montesi | 2/450 |
| 4,644,588 | 2/1987 | Zawacki | 128/858 |
| 4,677,974 | 7/1987 | Leonardi | 128/163 |
| 4,727,869 | 3/1988 | Leonardi | 128/163 |
| 4,790,031 | 12/1988 | Duerer | 128/858 |
| 4,797,956 | 1/1989 | Boyce | 128/858 |
| 4,907,580 | 3/1990 | Leonardi | 128/163 |
| 5,134,991 | 8/1992 | Hustead | 606/204 |
| 5,309,925 | 5/1994 | Policastro | 128/849 |

OTHER PUBLICATIONS

"Laser Protection Eyewear", *Wilson Ophthalmic Corporation Catalog*, p. 143–144, (Feb. 1998).

*Wilson Ophthalmic Corporation Catalog*, 4 pgs (including cover), (1997).

Kalra, L., et al., "The Effect of Nebulized Bronchodilator Therapy on Intraocular Pressures in Patients with Glaucoma", *Chest* 93(4), 739–741, (Apr. 1988).

Wilkinson, J.L., et al., "Intraocular Pressure and Eye Enlargement in Chicks", *Current Eye Research* 10(2), 163–168, (1991).

*Primary Examiner*—Michael A. Brown
*Attorney, Agent, or Firm*—Schwegman, Lundberg, Woessner & Kluth, P.A.

[57] ABSTRACT

A method and apparatus for preventing elevation of intraocular pressure during rest or sleep is disclosed. The apparatus comprises an eye covering device that is adapted to be comfortably worn during rest or sleep. The eye covering device bridges over the eyes and contacts the wearer's head along a nose bridge and an outer frame surrounding the eye sockets. When the wearer rolls onto his or her face during rest or sleep, pressure from an external object such as a pillow is imparted to the eye protection device rather than to the eyes. Accordingly, pressure on the eye during sleep is relieved.

8 Claims, 5 Drawing Sheets

METHOD AND APPARATUS FOR RELIEVING INTRAOCULAR PRESSURE

TECHNICAL FIELD

This invention relates generally to a method and apparatus for treating eye-related disorders and, more particularly, to eye protection for preventing application of external pressure to the eye and eyelid, especially during sleep.

BACKGROUND

While various eye disorders are related to elevated pressure within the eye, glaucoma is perhaps the most prevalent. Glaucoma is characterized by loss of optic nerve fibers, visual field loss (e.g., tunnel vision) and, if not effectively treated, by partial or total blindness of the affected eye.

While many types of glaucoma exist, most types are caused by chronic elevation of the intraocular pressure. The elevated pressure affects all parts of the eye. However, due to the specific anatomical location of the optic nerve and the delicate nature of the nerve tissue, it generally suffers the brunt of the disease. The loss of the nerve tissue, which typically occurs very slowly, results in an deformation of the nerve known as "cupping." As one might guess, a cupped nerve looks like it has been cupped out or excavated. While the effect of cupping on the visual function is directly related to the loss of tissue, symptoms of glaucoma may not appear until 50% or more of the nerve has been damaged. Unfortunately, once nerve damage has occurred, the loss is permanent. It is thus important to find these patients in the asymptomatic stage.

One common type of glaucoma is known as low tension glaucoma. Low tension glaucoma is a special, although common, type of nerve damage that demonstrates the characteristic cupping but does not have the measurable elevation of intraocular pressure that is associated with typical glaucoma. Accordingly, when the eye pressure is measured during clinic visits, it generally falls within the statistically normal range of between 10 and 22 mm Hg. Low pressure glaucoma has long baffled eye care professionals and has accordingly been the subject of much research. In particular, these investigations have evaluated how the eye damage occurs when the intraocular pressure appears normal. Emergent theories range from vascular insufficiency to the optic nerve to a peculiar susceptibility to even "normal" pressures.

It has been estimated that approximately 50% of all new cases of glaucoma can be characterized as low tension glaucoma. The failure of eye care professionals in the past to recognize that this glaucoma can occur even though intraocular pressure appears normal has led to blindness in countless people. Fortunately, modern medical practitioners are more aware and will generally diagnose the problem accurately.

The treatment of glaucoma generally involves lowering the pressure within the eye and thus relieving the nerve. Theoretically, this reduction in pressure will halt or slow the damage of the nerve fibers and hopefully slow or stop the loss of visual field and function.

The treatment modalities for high pressure and low tension glaucoma include: drugs (either topical eye drops or oral medications); laser therapy; or surgical procedures. While all of these methods have been useful in the treatment of high pressure glaucoma, total success has been elusive. This is partially due to the fact that progression of the nerve damage may continue despite what appears to be "successful" reduction of the intraocular pressure. With respect to the treatment of low tension glaucoma, the results have been even more disappointing.

Accordingly, there is a need for an improved method and apparatus for treating disorders of the eye resulting from elevated intraocular pressure.

SUMMARY

An apparatus and method for preventing external pressure on an eye is herein described. In one embodiment, eye contact is prevented by providing eye protection to intervene between an external object and the eye. This intervention prevents pressure which, absent the eye protection, would be imparted upon the eye by the external object. The eye protection is used consistently during rest or sleep to reduce eye disorders caused by long term or chronic elevated intraocular pressure.

The apparatus, in one embodiment, includes an attachment device for attaching the apparatus to a patient's head and eye protection means for intervening between an external object and the eye. The eye protection means includes force distribution means for distributing forces imparted by the external object on the eye protection means to the patient's head. The distribution of the forces is to a predetermined portion of the patient's head selected to avoid closing of blood vessels and to provide a comfortable fit when the external object contacts the eye protection means.

Advantageously, the present invention provides comfortable eye protection adapted for long term use. By attaching and wearing the eye protection on a consistent basis prior to rest or sleep, elevated intraocular pressure resulting from eye contact with external objects may be reduced or even eliminated. In turn, pressure-related eye disorders such as glaucoma may be effectively treated.

BRIEF DESCRIPTION OF THE DRAWINGS

The invention described herein will be further characterized with reference to the drawings, wherein.

DETAILED DESCRIPTION

Figure 1:
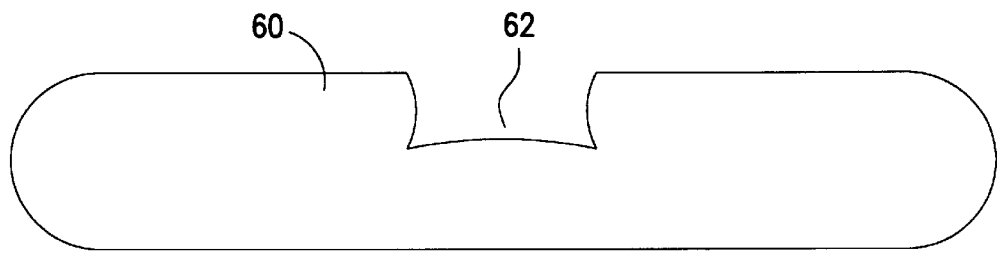
FIG. 1 is a perspective view of an eye protection apparatus in accordance with one embodiment of the invention.

In the following detailed description, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

While the exact causes of various eye disorders including high pressure and low tension glaucoma are not known, Applicant perceives that one possible explanation for the continued progression of "high" pressure glaucoma and a substantial cause of low tension glaucoma is pressure exerted on one or both eyes or eyelids during sleep. External pressure from a pillow or hand in contact with the eyelid will raise intraocular pressure to the same levels seen in "high" pressure glaucoma patients. Accordingly, treated "high" pressure glaucoma patients might experience repeated, chronic elevation of eye pressure during sleep, thus "undoing" the beneficial lowering their treatment has during waking hours. This phenomena may also explain how low tension glaucoma patients experience the "high" pressure that is the physiologic cause of cupping and nerve damage without showing any signs of elevated pressure during routine eye examinations.

The cumulative effects of intermittent or sleep-related pressure may therefore account for many glaucoma treatment failures. Untreated "high" pressure patients could be experiencing extreme elevations during sleeping hours, not only leading to cupping but also to obstruction of blood vessels and ultimately, blindness. Sleep-related pressure may also be a hidden cause of low tension glaucoma.

The present invention is directed to eye protection and a method to protect the eyes from pressure exerted by external objects, especially during sleep. The following discussion makes frequent reference to a "patient" or "wearer." These terms are used interchangeably and are intended to refer generally to a person using any embodiment of the invention as it is described herein or equivalents thereof. Furthermore, while the discussion is directed primarily to eye protection for humans, it is to be understood that the present invention, with minor modifications, may also be used with animals.

Broadly speaking, the eye protection and method described herein are adapted to prevent the eyes from directly contacting an external object such as a sleeping surface. Such direct contact may compress the eye and thus raise the internal eye pressure (i.e., intraocular pressure). While applicable to any situation in which the eye may be subjected to contact with an external object, Applicant perceives that the present invention is particularly beneficial during rest or sleep and the remainder of this discussion will focus on the same.

The term "sleeping surface" is hereinafter defined to include any surface which the eye may contact during rest or sleep. For purposes of this discussion, the sleeping surface generally comprises a pillow. However, other objects that may contact the eyes during sleep (e.g., sheets, blankets, mattress, hands, etc.) are also included.

In one embodiment, the eye protection includes means to encourage or compel sleep or rest in a supine position (i.e., on the patient's back) and avoid head movement. For example, the means to encourage may be a modified pillow 60 as shown in FIG. 1 having a depression 62 to cradle the head and prevent motion. Since the eyes are facing upwards, such a device prevents contact between the eyes and an external object. Alternatively, a helmet (not shown) having protrusions or weights which compel a supine orientation may similarly relieve external contact with the eyes.

Figure 2:
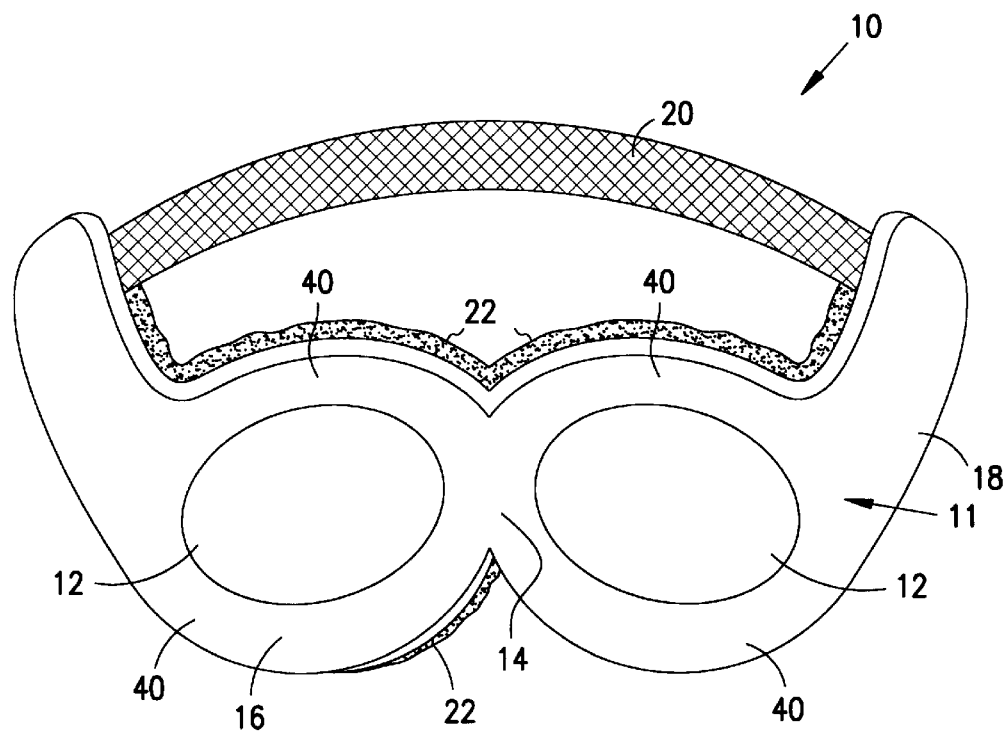
FIG. 2 is a perspective view of an eye protection apparatus in accordance with another embodiment of the invention.
Figure 3:
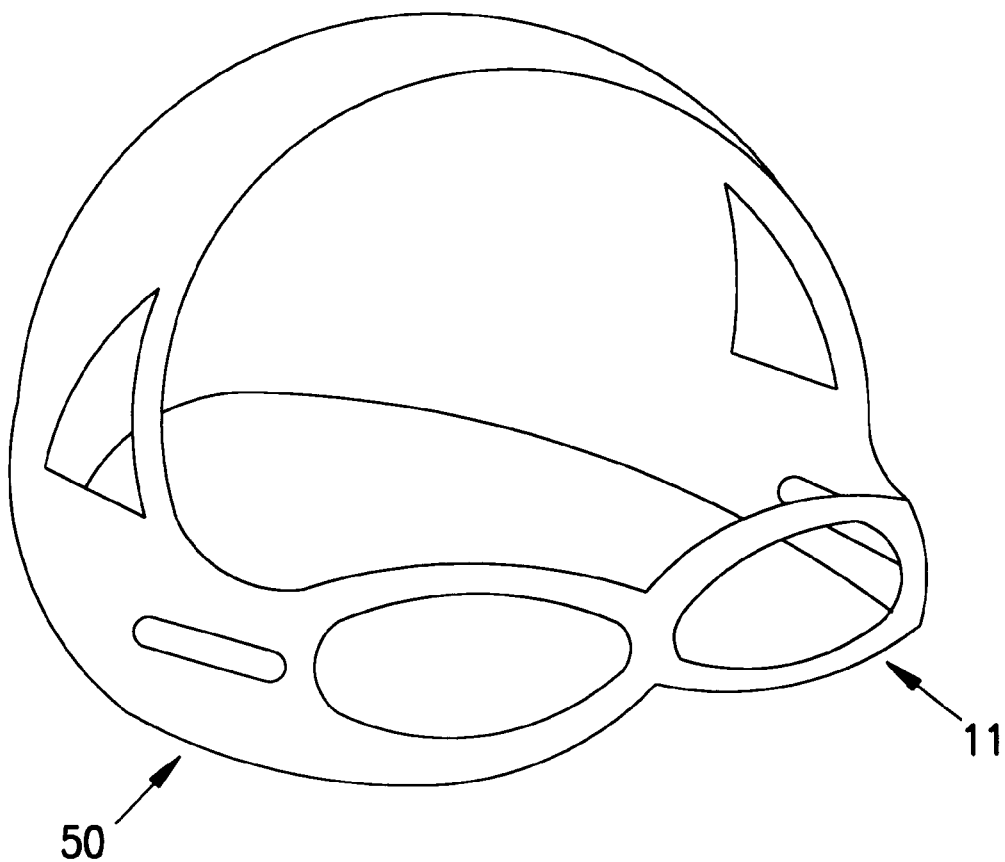
FIG. 3 is a perspective view of an eye protection apparatus in accordance with yet another embodiment of the invention.

In another embodiment, the eye protection includes eye protection means to alleviate pressure on the eyes even when sleeping in a face-down orientation. In one embodiment, the eye protection means is embodied in a goggle-type eye covering device 11 as shown in FIG. 2. In another embodiment, the eye protection means is part of a full or partial hat-like or helmet-like device 50 as shown in FIG. 3. In yet another embodiment, the eye protection means is embodied in a device similar to conventional eye glasses (not shown).

In addition to the eye protection means, the eye protection may also comprise attachment means to secure the eye protection means to the head. For instance, the attachment means, in one embodiment, comprises an attachment device such as an adjustable strap 20 as shown in FIG. 2 which extends around the head of the wearer. In another embodiment, the attachment means is part of a hat-like device or helmet 50 as shown in FIG. 3. In still yet another embodiment, the attachment means comprises rearwardly extending ear supports (not shown) similar to conventional eye glasses. The attachment means may also comprise other mechanical or adhesive features that may secure the device 11 to the wearer's head.

Although the eye protection may take many and varied forms as described above, for the sake of brevity it will be generally described hereinafter in terms of an eye protection apparatus 10 as generally depicted in FIG. 2 comprising the eye covering device 11 and the adjustable strap 20. However, it is noted that this particular embodiment is exemplary only and is not intended to limit the scope of the invention in any way.

Referring now to FIG. 2, the eye covering device 11 is made to be worn comfortably over the eyes during sleep. By bridging over the eye socket, it intervenes between the sleeping surface and the eye to prevent pressure to the latter. The eye covering device 11 comprises, in one embodiment, one or more eye guards or eye pieces 12 which are aligned over the eyes. The device 11 additionally comprises a nose bridge 14 and a frame 16. The nose bridge 14 connects the eye guards 12 and is designed to comfortably engage the nose of the wearer. In addition, the nose bridge 14 partially supports the eye covering device 11 over the wearer's face.

Figure 4:
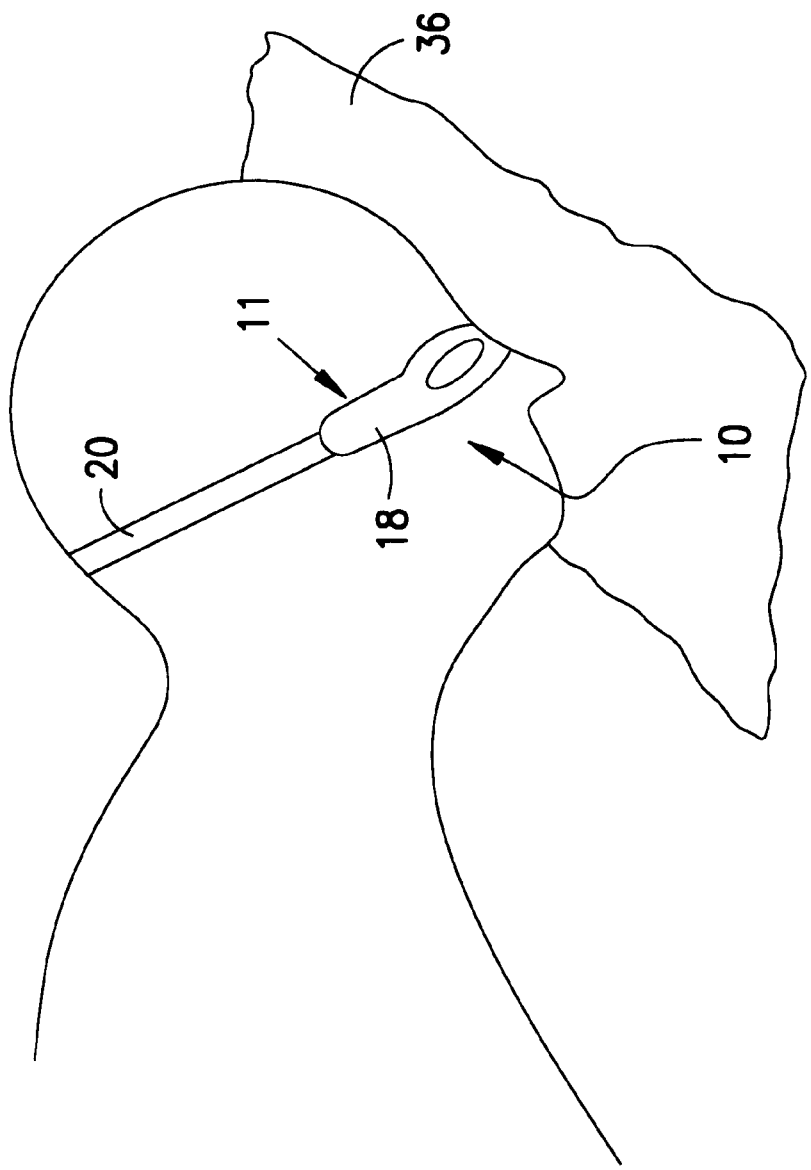
FIG. 4 illustrates the apparatus of FIG. 2 as it would be used during sleep.

The frame 16, in one embodiment, integrally includes the bridge 14 or, alternatively, the bridge 14 may be a separate, flexible or semi-flexible component that permits independent movement of each eye guard 12. In another embodiment, the frame 16 also includes wrap-around sections 18 which extend over the temple of the wearer as shown in FIG. 4. The adjustable strap 20 then extends between each wrap-around section 18 and secures the eye covering device 11 to the wearer's head.

The frame 16 surrounds the eye guards 12 and forms a force distribution means to distribute forces imparted from the sleeping surface away from the eyes and to the head of the wearer. In one embodiment, the device 11 distributes forces to the head at a periphery 40 of the frame 16. However, other force distributions means are possible. For example, the force distribution means may distribute forces to a different area or to a larger portion of the face or head.

In order to remain comfortable during rest or sleep, the eye protection apparatus 10 is generally a low profile device. That is, the device 11 and strap 20 protrude minimally from the face and head of the wearer. Comfort is further enhanced by the inclusion of padding 22 at various locations along the bridge 14 and the periphery 40 of the frame 16. In one embodiment, the padding is continuously located around the entire periphery 40. The padding 22 may be a breathable foam that permits perspiration to adequately evaporate from within the eye covering device 11. Alternatively, the padding 22 may be made from another soft, flexible material including, for example, rubber or cloth.

The eye guards 12 are, in one embodiment, translucent to permit generally unrestricted vision. In another embodiment, the eye guards 12 may be prescription lenses. In still yet another embodiment, the eye guards may be tinted or opaque to shade the wearer's eyes.

Having described various embodiments of the eye protection apparatus 10, the reader's attention is now directed to the use of the apparatus in reducing the occurrence of elevated intraocular pressure during rest or sleep. While the following discussion is directed primarily to the embodiment of the eye protection apparatus as shown in FIG. 2, the methods described below are equally applicable to the other devices (e.g., helmet, eye glasses, etc.) mentioned above. Accordingly, the following description is illustrative only and is not intended to limit the scope of the invention in any manner.

Referring once again to FIG. 4, the apparatus 10 is made to attach to the head of the wearer during sleep. As the wearer rolls onto his or her face, a pressure exerted by a pillow 36 (or other sleeping surface) that would normally be imparted to and reacted by the eyes is now imparted to the eye covering device 11 and distributed to the head as described below.

Figure 5:
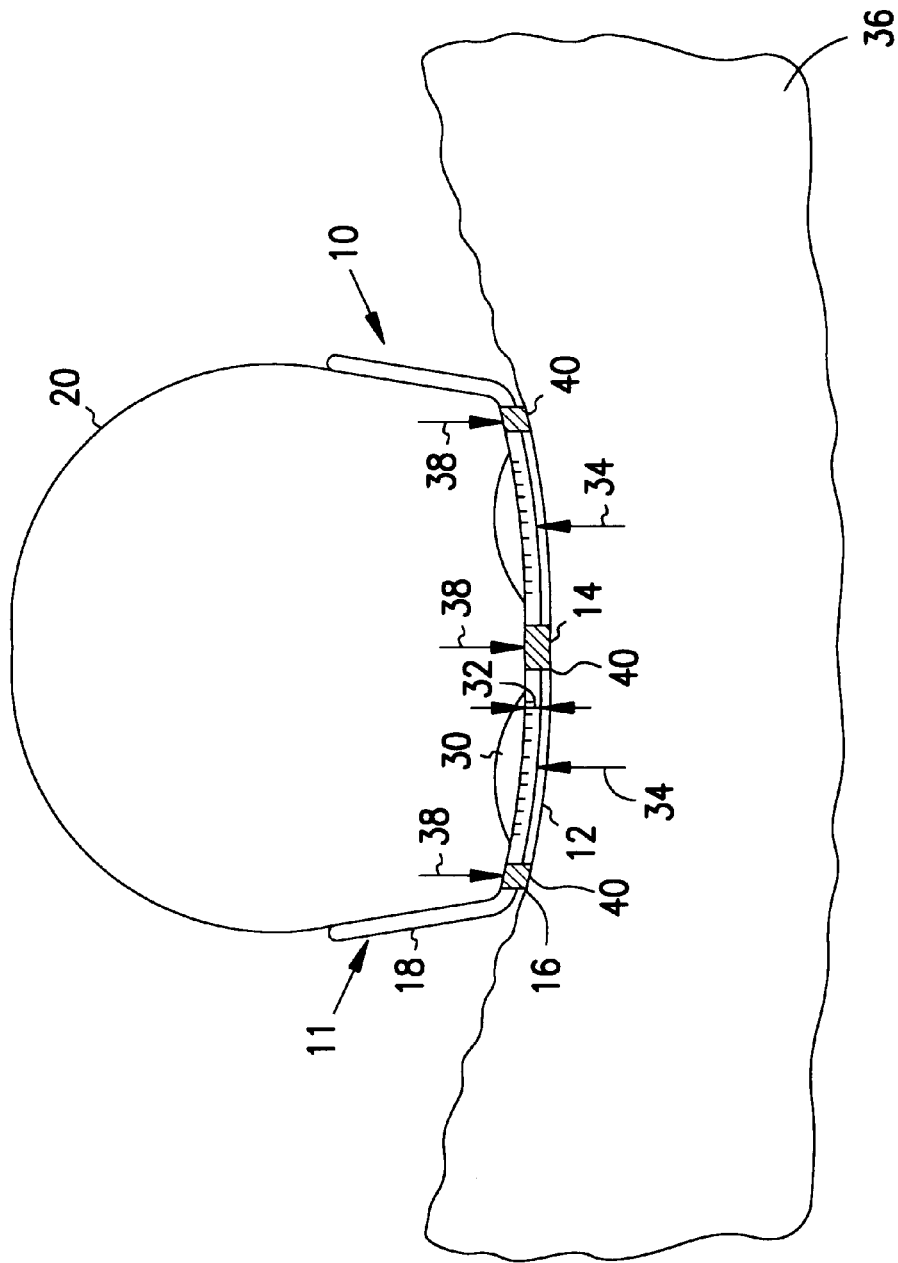
FIG. 5 is an end view of the apparatus of FIG. 4.
Figure 6:
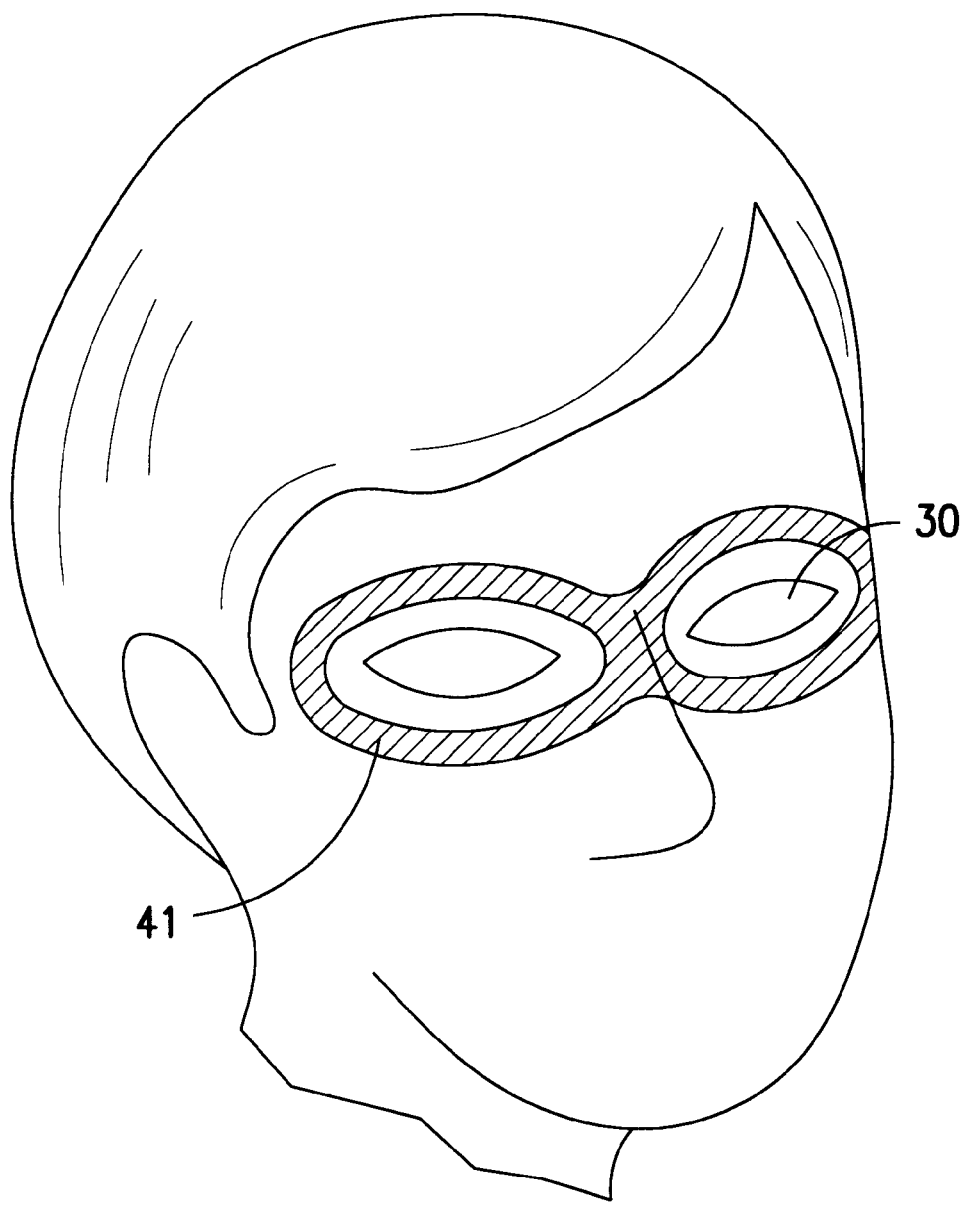
FIG. 6 is a perspective view of a user's face showing a potential contact zone for the periphery of the apparatus of FIG. 2.

Referring particularly to FIG. 5, the eye guards 12, supported by the frame 16 and bridge 14, are spaced away from the eyes 30 by a gap 32. When the wearer rolls onto his or her face, the pillow 36 exerts an upward force that is equal and opposite to the downward force—or weight—of the head. The distribution of the upward force over the entire face produces a facial pressure. A portion of this facial pressure, hereinafter denoted the external eye pressure 34, is normally imparted to the eyes. If the eyes are subjected to such an external pressure, the pressure within the eyes will increase, potentially resulting in pressure-related eye disorders. However, when the eye protection apparatus 10 is worn, the pressure 34 is instead imparted to the eye guards 12 and portions of the frame 16. The product of the pressure 34 and the frontal area (i.e., the area of the device 11 subjected to the pressure 34) yields a total force on the device 11. This total force is, in one embodiment, distributed to and reacted by a predetermined portion of the head as diagrammatically represented by the arrows 38 in FIG. 5. While shown two-dimensionally in FIG. 5, the total force is actually distributed over the entire periphery 40 of the frame 16. FIG. 6 shows a facial contact zone 41 for one embodiment of the periphery 40.

Although the eye guards 12 protect the eyes themselves, the periphery 40 adequately distributes the total force to the head in such a way that undue pressure on nearby nerves and blood vessels is prevented and comfort is maintained. Accordingly, it is advantageous to provide a relatively large periphery 40 so that the total force is distributed over a large contact zone 41. The larger the periphery 40, the lower the average pressure applied to the face and head.

The exact size and location of the periphery 40 as well as the overall fit of the device 10 is anatomically optimized to ensure comfort and reduce potentially adverse affects on local nerves and blood vessels. For example, an optician, ophthalmologist, or optometrist may custom-make the frame to conform to the wearer's face. In one embodiment, the frame 16 is made from lightweight plastic that can be formed and molded through application of heat. The tools necessary to heat the frame are present in most optical dispensaries as well as optometry and ophthalmology offices.

In another embodiment, the frame 16 is pliable so that relatively few sizes will accommodate the facial features of a broad range of patients.

In addition to providing a comfortable eye covering device 11, the apparatus 10 also includes a comfortable strap 20. The strap 20, in one embodiment, is made from a thin, soft material such as an elastic-cotton blend. The strap is of sufficient width to stabilize the device 11 and prevent strap rolling or twisting as the wearer moves during sleep. The fit, strap tension, and overall comfort of the apparatus 10 can be checked at both initial and follow-up visits to the optometrist or ophthalmologist.

Because comfort and fit are perceived to promote consistent long term use, the apparatus 10, in one embodiment, is best provided as a prescription optical device dispensed to patients having pressure-related eye disorders. By limiting availability to prescriptions, trained personnel may take certain precautions to ensure comfort and safety (avoidance of blood vessel/nerve interference). However, over-the-counter versions of the apparatus 10 are also possible within the scope of the invention.

Advantageously, the present invention provides comfortable eye protection adapted for long term use. By attaching and wearing the eye protection on a consistent basis prior to rest or sleep, elevated intraocular pressure resulting from eye contact with external objects may be reduced or even eliminated. In turn, pressure-related eye disorders such as glaucoma may be effectively treated.

Those skilled in the art will recognize that many embodiments are possible within the scope of the invention. Variations, modifications, and combinations of the various parts and assemblies can certainly be made and still fall within the scope of the invention. Thus, the invention is limited only by the following claims, and equivalents thereto.

What is claimed is:

1. A method for protecting an eye, the method comprising:
   providing eye protection to intervene between an external object and the eye to prevent pressure which, absent the eye protection, would be imparted upon the eye by the external object, the eye protection used consistently during rest or sleep to reduce the occurrence of eye disorders caused by long term or chronic elevated intraocular pressure.

2. The method of claim 1 wherein the eye protection comprises a goggle-type eye covering device.

3. The method of claim 1 wherein the eye protection comprises a helmet device.

4. The method of claim 1 wherein the eye protection comprises encouraging a supine position.

5. The method of claim 4 wherein the eye protection comprises a head restraint to prevent movement of the head.

6. The method of claim 1 further comprising prescribing the eye protection to patients having pressure-related disorders of the eye.

7. The method of claim 1, further comprising marketing the eye protection for use by patients having pressure-related disorders of the eye.

8. The method of claim 1 further comprising prescribing the eye protection to patients having pressure-related disorders of the eye, wherein the eye protection comprises:
   an attachment device for attaching the eye protection to the patient's head; and
   an eye covering device to intervene between the external object and the eye, the eye covering device including a frame for distributing pressure imparted by the external object on the eye covering device to the patient's head, wherein the distribution of the forces is to a predetermined portion of the head, said predetermined portion of the head selected to avoid closing of blood vessels and to provide a comfortable fit when the external object contacts the eye covering device.

\* \* \* \* \*

UNITED STATES PATENT AND TRADEMARK OFFICE
CERTIFICATE OF CORRECTION

PATENT NO. : 6,155,261
DATED : December 5, 2000
INVENTOR(S) : Day

It is certified that error appears in the above-identified patent and that said Letters Patent is hereby corrected as shown below:

Supplemental NOA mailed 10/12/2000 indicates that claims 1-8 and 18 were allowed. Claim 18 was not printed in the published patent.
    Please insert after claim 8,
-- 18.    A method comprising marketing eye protection for consistent use during rest and sleep for reduction of eye disorders, comprising:
    an attachment device for attaching the eye protection to a patient's head; and
    an eye covering device to intervene between an external object and the eye, the eye covering device including force distribution means for distributing forces imparted by the external object on the eye covering device to the patient's head, wherein the distribution of the forces is to a predetermind portion of the head, said predetermined portion of the head selected to avoid closing of blood vessels and to provide a comfortable fit when the external object contacts the eye covering device. --

Signed and Sealed this

Fourth Day of December, 2001

Attest:

*Nicholas P. Godici*

Attesting Officer

NICHOLAS P. GODICI
*Acting Director of the United States Patent and Trademark Office*